(12) United States Patent
Schmetterer et al.

(10) Patent No.: US 12,209,952 B2
(45) Date of Patent: Jan. 28, 2025

(54) METHODS AND SYSTEMS FOR POLARIZATION-SENSITIVE OPTICAL COHERENCE TOMOGRAPHY

(71) Applicant: Singapore Health Services Pte Ltd, Singapore (SG)

(72) Inventors: Leopold Schmetterer, Singapore (SG); Xinyu Liu, Singapore (SG)

(73) Assignee: Singapore Health Services Pte Ltd, Singapore (SG)

( * ) Notice: Subject to any disclaimer, the term of this patent is extended or adjusted under 35 U.S.C. 154(b) by 125 days.

(21) Appl. No.: 18/245,531

(22) PCT Filed: Sep. 17, 2021

(86) PCT No.: PCT/SG2021/050566
§ 371 (c)(1),
(2) Date: Mar. 15, 2023

(87) PCT Pub. No.: WO2022/060300
PCT Pub. Date: Mar. 24, 2022

(65) Prior Publication Data
US 2023/0358669 A1 Nov. 9, 2023

(30) Foreign Application Priority Data

Sep. 17, 2020 (SG) .......................... 10202009128V

(51) Int. Cl.
*G01N 21/23* (2006.01)
*G01B 9/02091* (2022.01)
(Continued)

(52) U.S. Cl.
CPC ......... *G01N 21/23* (2013.01); *G01B 9/02091* (2013.01); *G01N 21/21* (2013.01);
(Continued)

(58) Field of Classification Search
CPC ........ G01J 4/00; G01J 4/02; G01J 4/04; G01J 9/02; G01J 2009/0211; G01N 21/21;
(Continued)

(56) References Cited

U.S. PATENT DOCUMENTS

| | | | |
|---|---|---|---|
| 4,932,783 A | 6/1990 | Kersey et al. | |
| 5,102,222 A * | 4/1992 | Berger | G01J 4/04 356/365 |

(Continued)

OTHER PUBLICATIONS

Baumann B. et al., Peripapillary Rat Sciera Investigated in Vivo with Polarization-Sensitive Optical Coherence Tomography. Investigative Ophthalmology & Visual Science, Nov. 30, 2014, vol. 55, No. 11, pp. 7686-7696.

(Continued)

*Primary Examiner* — Gordon J Stock, Jr.
(74) *Attorney, Agent, or Firm* — Knobbe, Martens, Olson, & Bear, LLP

(57) ABSTRACT

A system for polarization-sensitive optical coherence tomography (PS-OCT) of a sample comprises an interferometric arrangement comprising a reference arm and a sample arm, the sample arm being arranged to emit optical radiation towards the sample; a phase modulation system arranged at an input to the sample arm; and a detector arranged to detect a signal generated by interference between a reference beam from the reference arm and a sample beam from the sample arm. The phase modulation system comprises: an electro-optic modulator; a polarizer arranged at a rotation angle relative to the fast axis of the electro-optic modulator; and a signal generator for delivering a driving voltage to the electro-optic modulator; wherein the rotation angle and the driving voltage are selected such that the phase modulation system generates three mutually orthogonal polarization states.

21 Claims, 9 Drawing Sheets

(51) Int. Cl.
*G01N 21/21* (2006.01)
*G01N 21/47* (2006.01)
*G02F 1/01* (2006.01)

(52) U.S. Cl.
CPC ........ *G01N 21/4795* (2013.01); *G02F 1/0136* (2013.01); *G01B 2290/70* (2013.01); *G02F 2203/50* (2013.01)

(58) Field of Classification Search
CPC ............... G01N 21/23; G01N 21/4795; G01N 2021/1787; G01B 9/02091; G01B 9/02011; G01B 2290/70
See application file for complete search history.

(56) References Cited

U.S. PATENT DOCUMENTS

| | | | | |
|---|---|---|---|---|
| 5,245,408 | A * | 9/1993 | Cohen | G01J 9/02 356/491 |
| 6,798,558 | B2 * | 9/2004 | Hayashi | G02F 3/00 398/154 |
| 6,885,882 | B2 * | 4/2005 | Cote | G01N 21/21 600/319 |
| 7,016,048 | B2 | 3/2006 | Chen et al. | |
| 7,280,770 | B2 * | 10/2007 | Tan | H04B 10/64 398/205 |
| 7,970,458 | B2 * | 6/2011 | Norris | A61B 18/22 600/478 |
| 8,570,527 | B2 * | 10/2013 | Milner | G01B 9/02091 356/497 |
| 8,780,433 | B2 * | 7/2014 | Yao | G02F 1/0136 359/290 |
| 9,471,277 | B2 * | 10/2016 | Yasuno | G01B 9/02027 |
| 9,863,869 | B2 * | 1/2018 | Yasuno | A61B 3/102 |
| 10,478,253 | B2 * | 11/2019 | Mak | A61B 5/0066 |
| 11,473,897 | B2 * | 10/2022 | Bouma | G01B 9/02091 |
| 2006/0132790 | A1 | 6/2006 | Gutin | |
| 2008/0013093 | A1 | 1/2008 | Izatt et al. | |
| 2017/0074638 | A1 * | 3/2017 | Fukuhara | G01B 9/02091 |
| 2017/0160148 | A1 | 6/2017 | Saeki | |
| 2017/0199116 | A1 | 7/2017 | Yasuno et al. | |
| 2018/0014730 | A1 * | 1/2018 | Lee | A61B 5/00 |

OTHER PUBLICATIONS

Saxer C. E. et al., High-speed fiber-based polarization-sensitive optical coherence tomography of in vivo human skin. Optics Letters, Sep. 15, 2000, vol. 25, No. 18, pp. 1355-1357.
International Search Report in PCT/SG2021/050566 dated Mar. 24, 2022 in 4 pages.
Written Opinion of Search Authority in PCT/SG2021/050566 dated Mar. 24, 2022 in 5 pages.

* cited by examiner

METHODS AND SYSTEMS FOR POLARIZATION-SENSITIVE OPTICAL COHERENCE TOMOGRAPHY

TECHNICAL FIELD

The present disclosure relates generally to methods and systems for polarization-sensitive optical coherence tomography (PS-OCT), for example (but not exclusively) in the field of ophthalmology.

BACKGROUND

Optical coherence tomography (OCT) is a well-established imaging modality that allows for high-resolution cross-sectional and three-dimensional imaging of translucent tissues. Intensity based OCT is the standard approach of OCT imaging and does not provide a tissue-specific contrast. Polarization sensitive (PS) OCT produces contrast via the birefringent properties of tissues. PS-OCT is therefore based on the additional detection of the polarization state of light, thereby providing additional information.

In ophthalmology, PS-OCT has been used to image the anterior segment as well as the posterior segment of the eye. In glaucoma, the technique has been proposed for the evaluation of the bleb after trabeculectomy surgery and for imaging the trabecular meshwork. In corneal imaging, it has been proposed for early detection and staging of keratoconus. At the posterior pole, it has been used to quantify the retinal nerve fiber layer, for contrasting the retinal pigment epithelium, and for quantification of drusen volume and drusen area. Recently, PS-OCT has also been used to study the birefringent properties of the sclera in animal models, particularly during an experimental increase in intraocular pressure (IOP).

Measurement of true 3D tissue structure inside the eye requires explicitly knowing the full Mueller matrix of the tissue, because diattenuation happens at the cornea-air interface. A full 4×4 Mueller matrix has three distinct eigenvalues and thus needs three measurements. However, current PS-OCT systems are limited to using two polarization states as the illumination light states. Such systems can provide a contrast of tissue polarimetry properties, but are not capable of measuring the true three-dimensional structure of the tissue.

One application of PS-OCT is in imaging of the sclera, which is the outermost layer of the eye. The sclera protects the interior ocular structures and determines the final shape and size of the globe. The sclera is predominantly made up of collagen, with fibroblasts that produce its extracellular matrix (ECM). During the development and progression of myopia, the sclera undergoes thinning and weakening, associated with re-organization of the collagen fibre. Structural and biomechanical changes in the myopic sclera are well documented, including progressive thinning, reduction of glycosaminoglycan and collagen contents, and disorganization of fibril assembly. These anatomical changes are associated with alterations in biomechanical property of the sclera such as creep rate, which represents the extension of the sclera over time when a constant or dynamic load is applied.

ECM structure dominates the biomechanical properties of the sclera. During the past few decades, ex vivo tools, including wide-angle X-ray scattering, small-angle light scattering, multiphoton microscopy, polarized light microscopy, magnetic resonance imaging, scanning electron microscopy, transmission electron microscopy and atomic force microscopy, have been established to examine the sclera. This has greatly increased the understanding of the fine structure of the ECM at multiple scales associated with different stages of myopia progression. However, all of these tools require the removal of the eyeball, resulting in potential tissue preparation distortion. More importantly, though ex vivo studies have shown change of biomechanical properties in myopia progression, the lack of high resolution, 3D imaging tools has hindered the clinical evaluation of sclera change in patients in vivo.

Currently, there is a lack of imaging-based biomarkers for the progression of myopia. It has been shown that children undergoing faster axial eye growth exhibit less thickening of the choroid over time, but the association is too weak to be considered as a true biomarker. This is linked to a number of problems in clinical decision making. First, it is currently unknown which children that start to develop myopia will develop pathological myopia in the future. This is particularly important when it comes to the decision of initialization of atropine treatment or other interventions to slow down the progression of axial eye growth.

It would be desirable to address one or more of the above difficulties.

SUMMARY OF THE PRESENT DISCLOSURE

The present disclosure relates to a system for polarization-sensitive optical coherence tomography (PS-OCT) of a sample, comprising:
 an interferometric arrangement comprising a reference arm and a sample arm, the sample arm being arranged to emit optical radiation towards the sample;
 a phase modulation system arranged at an input to the sample arm; and
 a detector arranged to detect a signal generated by interference between a reference beam from the reference arm and a sample beam from the sample arm;
 wherein the phase modulation system comprises:
  an electro-optic modulator;
  a polarizer arranged at a rotation angle relative to the fast axis of the electro-optic modulator; and
  a signal generator for delivering a driving voltage to the electro-optic modulator;
  wherein the rotation angle and the driving voltage are selected such that the phase modulation system generates three mutually orthogonal polarization states.

The rotation angle may be between about 17.6 degrees and about 38.1 degrees, and in particular may be about 27.3678 degrees.

The driving voltage may have a sawtooth waveform, such as a 3-point step driving waveform, in which the steps correspond to modulation depths of −120 degrees, 0 degrees, and 120 degrees.

The system may comprise at least one processor that is configured to determine the Mueller matrix of the sample from the signal detected by the detector. In one example, the at least one processor may be configured to determine a diattenuation contribution to the Mueller matrix by polar decomposition. In another example, the at least one processor is configured to determine birefringence of the sample based on the Mueller matrix. The at least one processor may be configured to apply a constraint to the determination of the birefringence of the sample based on a priori knowledge of one or more structural parameters of the sample.

The present disclosure also relates to a phase modulation system for polarization-sensitive optical coherence tomography (PS-OCT) of a sample, the phase modulation system being positionable at an input of a sample arm that is arranged to emit optical radiation towards the sample, the phase modulation system comprising:
an electro-optic modulator;
a polarizer arranged at a non-zero rotation angle relative to the fast axis of the electro-optic modulator; and
a signal generator for delivering a driving voltage to the electro-optic modulator;
wherein the rotation angle and the driving voltage are selected such that the phase modulation system generates three mutually orthogonal polarization states.

The present disclosure further relates to a method of polarization-sensitive optical coherence tomography (PS-OCT) of a sample, comprising:
generating, by sample arm optics, a sample beam for illuminating the sample; and
detecting an interference signal generated by interference of the sample beam with a reference beam;
wherein the sample arm optics have a phase modulation system arranged at an input thereof, the phase modulation system being configured to:
transmit an input beam through a polarizer arranged at a rotation angle relative to the fast axis of an electro-optic modulator; and
deliver a driving voltage to the electro-optic modulator;
wherein the rotation angle and the driving voltage are selected such that the phase modulation system generates three mutually orthogonal polarization states.

The rotation angle may be between about 17.6 degrees and about 38.1 degrees, in particular about 27.3678 degrees.

As for the above-mentioned system, the driving voltage may have a sawtooth waveform, for example a 3-point step driving waveform as disclosed above.

The method may comprise determining the Mueller matrix of the sample from the interference signal.

In some embodiments, the method may comprise determining a diattenuation contribution to the Mueller matrix by polar decomposition.

The method may comprise determining birefringence of the sample based on the Mueller matrix. A constraint may be applied to the determination of the birefringence of the sample based on a priori knowledge of one or more structural parameters of the sample.

In some embodiments, the sample is an eye; and the method may further comprise generating a fiber anisotropy image and/or a fiber orientation image of the sclera of the eye. In this case, a constraint that the fiber collagen is circumferential around the optical nerve head on the sclera may be applied when determining birefringence of the sample.

The present disclosure further relates to a method of modulating a sample beam for polarization-sensitive optical coherence tomography (PS-OCT) of a sample, comprising:
arranging a phase modulation system at an input of sample arm optics of a PS-OCT system, the phase modulation system being configured to:
transmit an input beam through a polarizer arranged at a rotation angle relative to the fast axis of an electro-optic modulator; and
deliver a driving voltage to the electro-optic modulator;
wherein the rotation angle and the driving voltage are selected such that the phase modulation system generates three mutually orthogonal polarization states.

BRIEF DESCRIPTION OF THE DRAWINGS

Some embodiments of a PS-OCT system and method, in accordance with present teachings will now be described, by way of non-limiting example only, with reference to the accompanying drawings in which.

DETAILED DESCRIPTION

Figure 1:
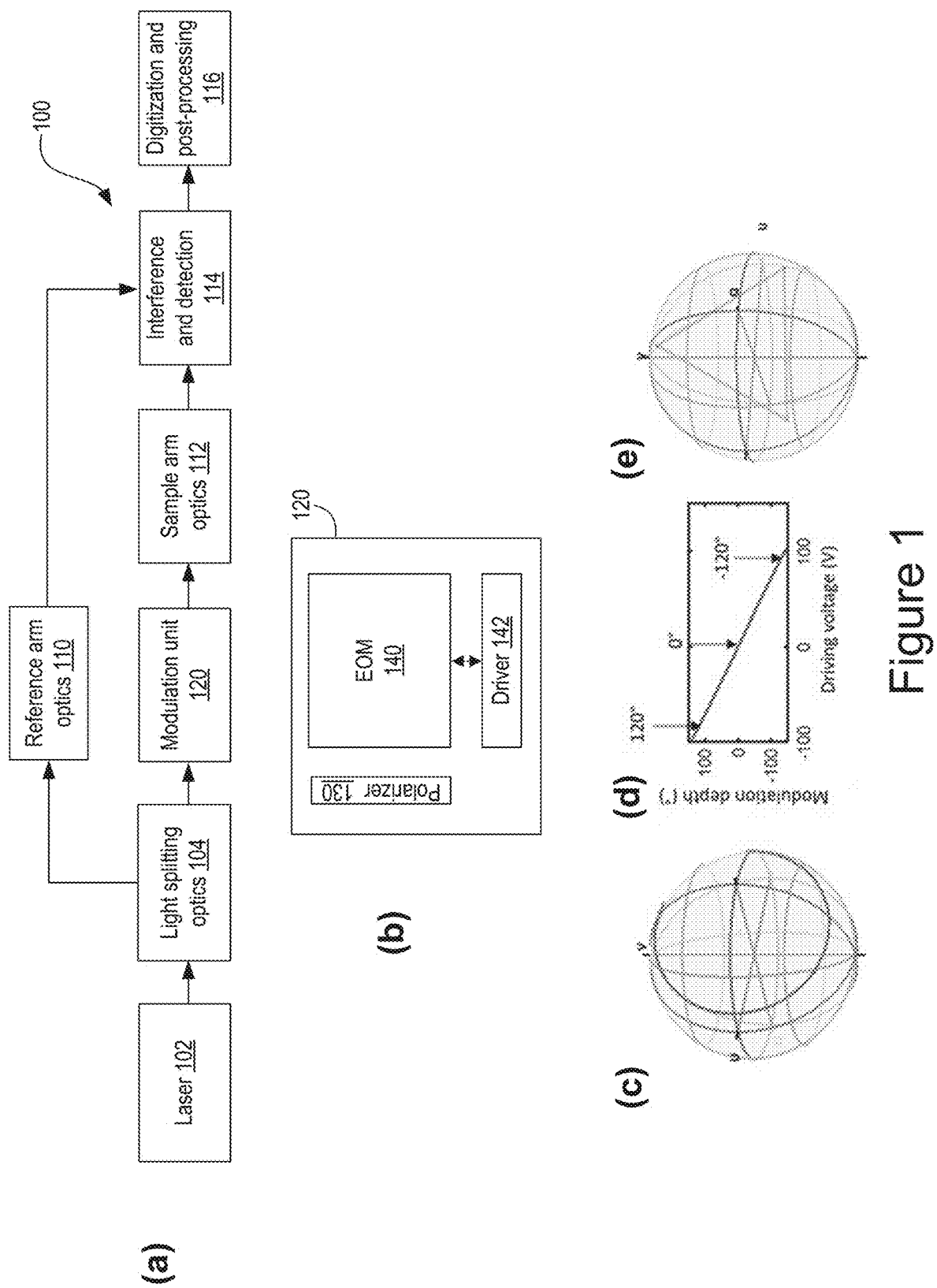
FIG. 1(a) is a block diagram of a PS-OCT system consistent with embodiments of the present disclosure.
FIG. 1(b) is a block diagram of a modulation unit of the system of FIG. 1(a)
FIG. 1(c) shows a Poincaré sphere showing the modulation state evolution of a ramp voltage for the modulation unit of FIG. 1(b)
FIG. 1(d) shows the relationship between the driving voltage and modulation depth for the modulation unit of FIG. 1(b)
FIG. 1(e) shows a Poincaré sphere with output states of the modulation unit.

Embodiments of the present disclosure provide a system and method to image high resolution, 3D scleral ECM collagen structure in vivo. Embodiments make use of a novel modulation apparatus that can be added to existing PS-OCT technology. Although embodiments are described with reference to their use in ophthalmic imaging, it will be appreciated that the technology of the present disclosure is applicable in other contexts, including non-ophthalmic medical imaging, and even non-medical imaging.

For example, applying the modulation apparatus to an ophthalmic PS-OCT, full Mueller properties of the sclera can be measured. With the full Mueller matrix, the polarization modification of the air-cornea interface can be compensated, and depolarization, diattenuation and retardation can be extracted as additional contrasts, and the three-dimensional structure of the sclera can be reconstructed at micron-scale resolution. Derived metrics from the scleral volume measurement, including the collagen anisotropy of the posterior pole, can serve as new biomarkers for myopia screening and diagnosis, as well as for other diseases involving the sclera such as glaucoma or posterior scleritis.

In embodiments, a modulation apparatus is used on the light input portal of a PS-OCT. The modulation apparatus can generate 3 eigen-polarization states and enables the PS-OCT to time-multiplex measure the full Mueller matrix of the specimen under examination at high speed (faster than 200 kHz), thereby enabling extraction of the birefringence and structure information based on computational reconstruction.

FIG. 1(a) is a schematic diagram of an example PS-OCT system 100 consistent with embodiments of the present disclosure. The PS-OCT system 100 comprises a swept source laser 102 that is split by light splitting optics 104 to feed reference arm optics 110 and sample arm optics 112. Contrary to conventional PS-OCT systems, the system 100 comprises a modulation unit 120 that is positioned to receive an input optical signal from the light splitting optics 104, modulate the input signal to generate an output signal that comprises three orthogonal eigenstates, and to output the output signal to the sample arm optics 112. The light from the sample arm 112 and reference arm 110 is then combined and detected by interference and detection unit 114, and digitized and analyzed by digitization and post-processing unit 116. The digitization and post-processing unit may comprise one or more processors configured to carry out various post-processing and image reconstruction operations, including determination of the full Mueller matrix of the sample, as will be described in further detail below.

As shown in FIG. 1(b), the modulation unit comprises a polarizer 130 placed in front of an electro-optic modulator (EOM) 140 that is driven by driver module 142. The polarizer 130 is optimally placed at 17.6322°, or positioned at an angle of 27.3678° relative to the fast axis of the EOM 140. At this angle, the EOM 140 is caused to generate three eigenstates that represent three vectors on the Poincaré sphere that are mutually perpendicular, or orthogonal in Poincare space. In the Poincaré polarization representation, an EOM 140 evolves the light state to a circle on the Poincaré sphere, as shown in FIG. 1(c). With a polarizer 130 placed at 17.6322°, the radius of the circle is determined as the square root of (2/3), meaning that three equally dividing points of this particular circle principally represent three eigenstates.

FIG. 1(d) shows the relationship between the modulation depth and the driving voltage. A lower refractive index is encountered by light polarized along the fast axis, when compared with light polarized along another, slow axis. The light polarized along the fast axis therefore travels faster through the EOM than light polarized along a slow axis. The phase shift between the fast axis and slow axis is the modulation depth. Three points corresponding to modulation depth of 120°, 0°, −120° are used to form a three-point step driving waveform. These correspond to the mutually perpendicular eigenstates. FIG. 1(e) shows the Poincaré sphere representation of the modulation output from the modulation unit 120.

Figure 2:
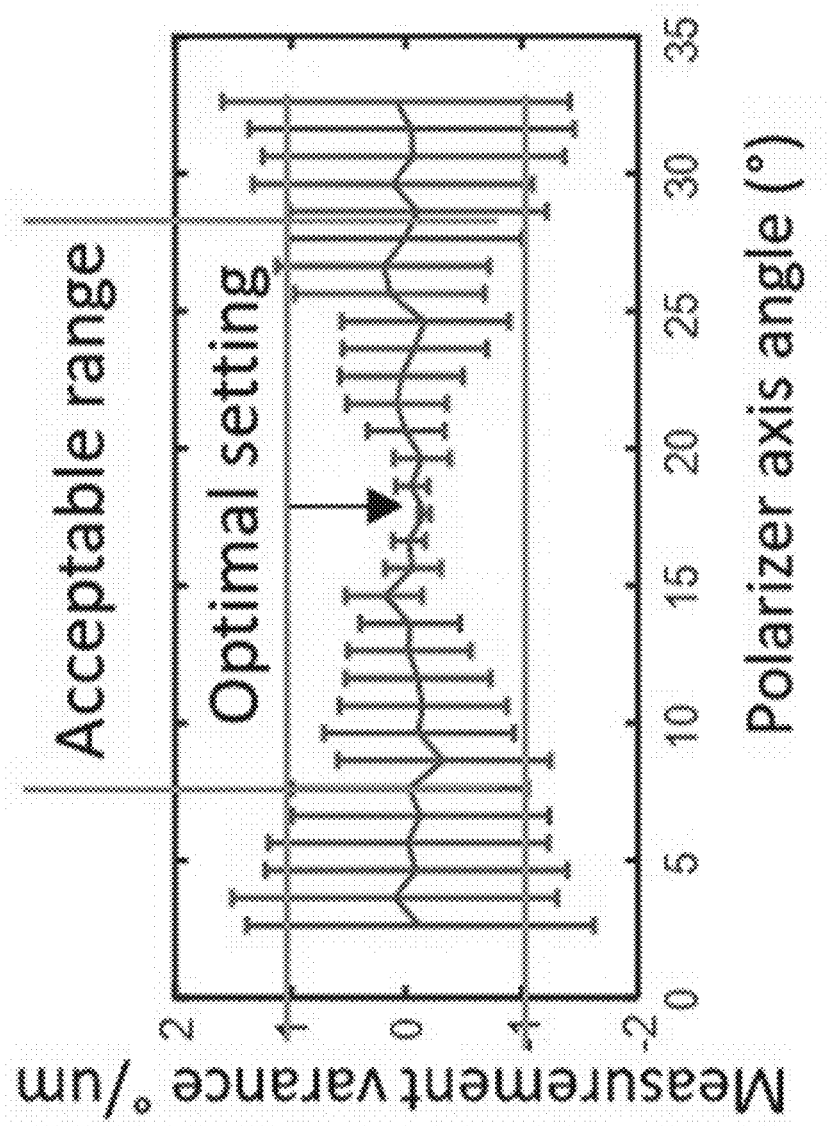
FIG. 2 shows the dependence of measurement error on polarizer axis angle.

It is possible for the polarizer 130 to be oriented at angles other than the optimal angle of 17.6322°. This is illustrated in FIG. 2, which shows the measurement error at angles that are different to this number. An experiment was conducted with different orientation angles using a phantom with known birefringence as the sample. As the offset from the optimal angle increases, the variance of the measurement increases correspondingly. To maintain a meaningful measurement in the context of measurements of the sclera, an offset that is within +/−9.7 degrees is acceptable, as the variance of the measurement is smaller than the common birefringence of the human sclera (1 degree/micrometer). Therefore, recitation of a specific angle may be taken to include functionally comparable angles within the acceptable offset. Accordingly, in embodiments, the polarizer is optimally placed at 17.6322° and can have an angle of rotation in the range from 7.9322° to 27.3322°, resulting in larger penetration depth with longer wavelength. In some embodiments, the angle may be in the range from about 16.6 to 18.6 degrees; or about 15.6 to 19.6 degrees; or about 14.6 to 20.6 degrees; or about 13.6 to 21.6 degrees; or about 12.6 to 22.6 degrees; or about 11.6 to 23.6 degrees; or about 10.6 to 24.6 degrees; or about 9.6 to 25.6 degrees; or about 8.6 to 26.6 degrees.

Figure 3:
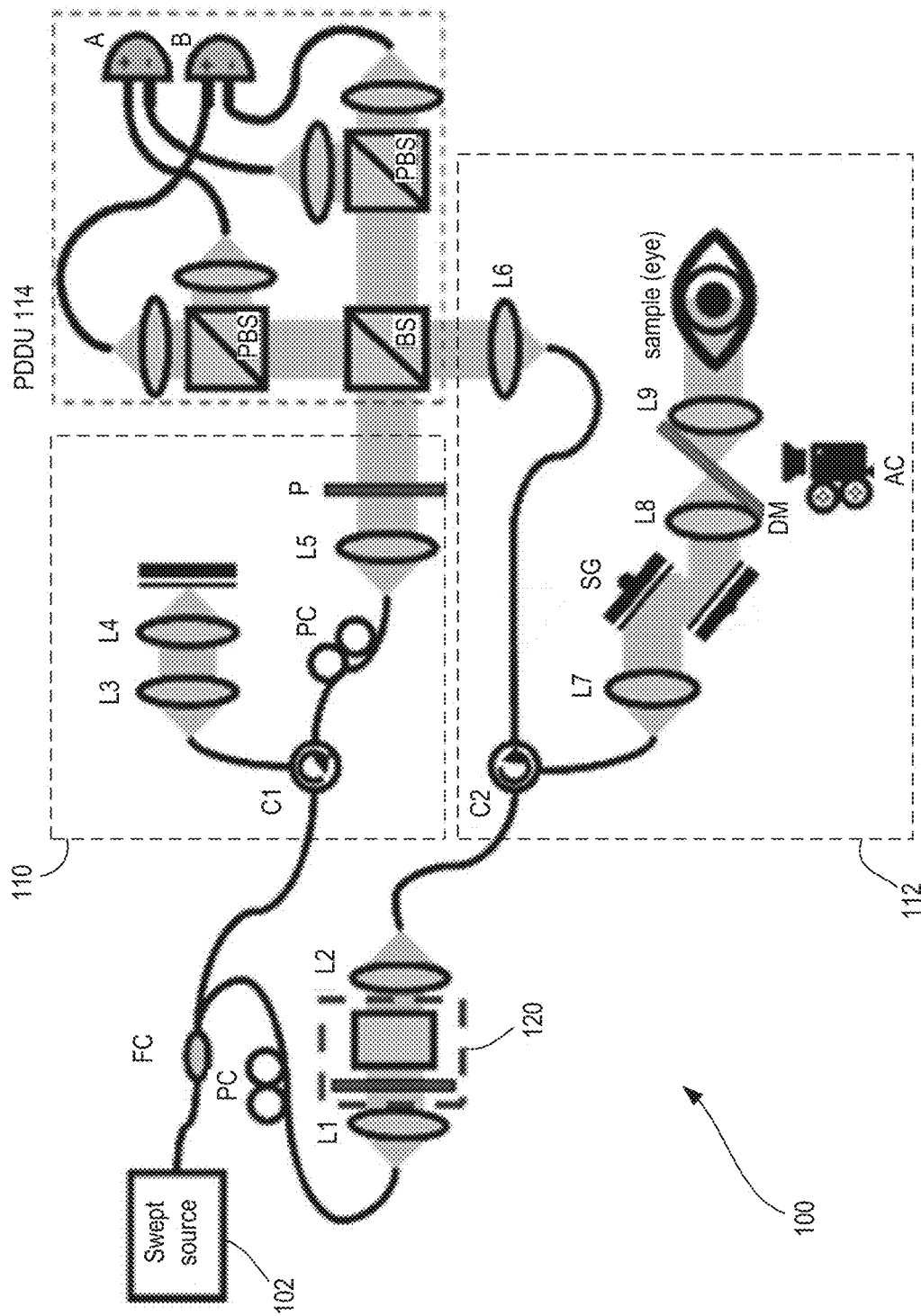
FIG. 3 shows one possible implementation of components of the PS-OCT system of FIG. 1(a)

Turning now to FIG. 3, a representative, but non-limiting, example of a PS-OCT system 100 consistent with that of FIG. 1 is shown. In the system 100, light from a swept source laser 102 is split at a fiber coupler (FC) and guided to reference arm 110, and to sample arm 112 via the modulation unit 120, and detected and digitized at a polarization diversity detection unit (PDDU) 114. Light is received at reference arm optical circulator C1 in the reference arm 110, from where it is transmitted to a collimating lens L3 and focusing lens L4 and focused onto a mirror that is mounted to a translation stage. Light reflected from the mirror then passes back through lenses L4 and L3 to the circulator C1 whereby it is transmitted to a polarization controller PC and then through to collimating lens L5, and through a linear polarizer P to the PDDU 114.

Light reaches the modulation unit 120 via a polarization controller (PC) and a collimating lens L1, and upon being modulated and emitted as described above, is transmitted to the sample arm 112 via a focusing lens L2. At the sample arm 112, the modulated output light is received at sample arm optical circulator C2, whereby it is transmitted to a collimating lens L7, and then on to a scanning galvanometer SG that enables xy-scanning of the sample (in this example, an eye)—in FIG. 3, DM refers to a dichroic mirror and AC refers to an alignment camera. Light that is backscattered from the sample then propagates back to circulator C2, whereby it exits the sample arm 112 via collimating lens L6 to the PDDU 114.

Determination of the Full Mueller Matrix

Once the polarization state of the light from the sample is detected by PDDU 114, it can be analyzed to determine the full Mueller matrix, as will now be described in detail.

Without loss of generality, the input probing light with three orthogonal inputs before going through the system and sample optics (i.e., after exiting modulation unit 120 and before entering sample arm 112) can be assembled into a probing matrix $M_{probing}$:

$$M_{probing} = \begin{bmatrix} 1 & 1 & 1 \\ 1 & 0 & 0 \\ 0 & 1 & 0 \\ 0 & 0 & 1 \end{bmatrix}.$$

After going through the system and sample, represented by a Mueller matrix M, the probing light is detected by the PDD unit 114, which detects the polarization state of the received light in Stokes space as $[s_0\ s_1\ s_2\ s_3]^T$. The raw data received by the detector can be assembled into a detection matrix $M_{detecting}$:

$$M_{detecting} = M \cdot M_{probing},$$

where M is the 4×4 pure Mueller (Jones-Mueller) matrix of the overall light circuit:

$$M = \begin{vmatrix} m_{00} & m_{01} & m_{02} & m_{03} \\ m_{10} & m_{11} & m_{12} & m_{13} \\ m_{20} & m_{21} & m_{22} & m_{23} \\ m_{30} & m_{31} & m_{32} & m_{33} \end{vmatrix} = m_{00} \begin{bmatrix} 1 & D \\ m_R D & m_R m_D \end{bmatrix}.$$

Therefore, the detecting matrix can be obtained:

$$M_{detecting} = \begin{bmatrix} m_{00} + m_{01} & m_{00} + m_{02} & m_{00} + m_{03} \\ m_{10} + m_{11} & m_{10} + m_{12} & m_{10} + m_{13} \\ m_{20} + m_{21} & m_{20} + m_{22} & m_{20} + m_{23} \\ m_{30} + m_{31} & m_{30} + m_{32} & m_{30} + m_{33} \end{bmatrix}.$$

In terms of $D$ and $m_R$, $M_{detecting}$ can be expressed as $$M_{detecting} = m_{00} \begin{bmatrix} D^T + 1 \\ m_R D^M + m_R m_D \end{bmatrix},$$

where $D = [d_1 \; d_2 \; d_3]^T = [m_{01}/m_{00} \; m_{02}/m_{00} \; m_{03}/m_{00}]^T$. $D^M$ is defined as $$\begin{bmatrix} d_1 & d_2 & d_3 \\ d_1 & d_2 & d_3 \\ d_1 & d_2 & d_3 \end{bmatrix}.$$

The superscript $^T$ denotes the matrix transpose.

To solve $m_{00}$, an auxiliary matrix is constructed to remove the retarder in the measurement:

$$M_{aux} = M^T_{sub} M_{sub} = m_{00}^2 (D^M + m_D)^T m_R^T m_R (D^M + m_D)$$
$$= m_{00}^2 (D^M + m_D)^T (D^M + m_D).$$

The detecting matrix can be expressed as:

$$M_{detecting} = \begin{bmatrix} a & b & c \\ & Msub & \end{bmatrix},$$

where $a = m_{00}(d_1 + 1)$, $b = m_{00}(d_2 + 1)$, $c = m_{00}(d_3 + 1)$, $a,b,c > 0$.

Further simplifying $M_{aux}$:

$$M_{aux} = \begin{bmatrix} a^2 & ab - m_{00}^2 \sin2\kappa & ac - m_{00}^2 \sin^2\kappa \\ ab - m_{00}^2 \sin^2\kappa & b^2 & bc - m_{00}^2 \sin^2\kappa \\ ac - m_{00}^2 \sin^2\kappa & bc - m_{00}^2 \sin^2\kappa & c^2 \end{bmatrix}.$$

Note that $\cos^2\kappa = |D|^2$, $D = [(a-1)/m_{00}(b-1)/m_{00}(c-1)/m_{00}]^T$, and thus equations can be found from the entries in $M_{aux}$ and $D$, such as:

$$M_{aux}(1,2) = ab - m_{00}^2 (1 - |D|^2).$$

Although more than one equation can be found, they are redundant with each other. $m_{00}$ can be solved as:

$$m_{00} = (a + b + c - \sqrt{2ab + 2ac + 2bc - a^2 - b^2 - c^2 - 2\varepsilon})/2,$$

where $\varepsilon = (ab + bc + ac - M_{aux}(1,2) - M_{aux}(1,3) - M_{aux}(2,3))/3$.

Note $m_{00}$ is solved from a 2 order polynomial equation, which has 2 roots. Only the one listed above is valid.

Once $m_{00}$ is solved, $D$, $m_D$, $m_R$ can be reconstructed sequentially, and the 4×4 Mueller matrix $M$ of the tissue can then be reconstructed, as follows.

$$Msub = \begin{bmatrix} Q1 & Q2 & Q3 \\ U1 & U2 & U3 \\ V1 & V2 & V3 \end{bmatrix} = [S_I \; S_{II} \; S_{III}]$$

$$m_D = \sin\kappa I + (1 - \sin\kappa/\cos2\kappa)(D \otimes D^T)$$

$$m_R = \frac{1}{m00} Msub(D^M + m_D)^{-1}$$

$$M = m_{00} \begin{bmatrix} 1 & D \\ m_R D & m_R m_D \end{bmatrix}$$

The raw fringe data was recorded by the described system. Dispersion calibration was applied by optimizing a 3-order polynomial phase correction term that maximized the contrast of the magnitude of Fourier transform of the raw data. Phase variation from the laser was extracted from a calibration signal and compensated to the fringe. The full Mueller matrix of the sample was obtained from the sequentially measured Stokes vectors.

In the case of ophthalmic PS-OCT, a diattenuation term, which is mainly induced by the cornea, may be obtained by polar decomposition and removed from the sample Mueller matrix. The depth resolved birefringence can be resolved by the solution of the differential equation of the cumulative Mueller matrix M:

$$\frac{dM(2z)}{dz} = 2mM(2z)$$

$$m = \begin{bmatrix} 0 & LD & LD' & CD \\ LD & 0 & CB & -LB' \\ LD' & -CB & 0 & LB \\ CD & LB' & -LB & 0 \end{bmatrix}$$

where LB is linear birefringence, LD is linear diattenuation, CB is circular birefringence, and CD is circular diattenuation.

The solution form is a matrix exponential, $\exp(\beta x)$. The 3D vector $\beta$ describes the fiber structure of the underlying sample. Specifically, the Euclidean length of $\beta$ represents the fiber anisotropy and the direction of $\beta$ represents the fiber orientation. However, $\beta$ may not be solvable unless another constraint is added based on a priori knowledge of the sample. Accordingly, to recover the absolute fiber orientation, $\beta$ can be rotated by a factor $\exp(i\varphi)$ to meet the a priori condition that the fiber collagen is circumferential around the optical nerve head on the sclera. In some embodiments, it will be appreciated that absolute direction may not be important, such that a constraint based on a priori knowledge need not be applied. In this case, the overall measurement will be randomly offset by a phase factor $\exp(i\varphi)$, but a map showing information indicative of relative orientation of objects within the image may still be produced.

Experimental Results

An example system was constructed in accordance with the present invention. Chick and guinea pig models were investigated. A cohort of 10 chicken and 4 guinea pigs were studied. Myopia was induced by covering a diffuser on the experimental eye, while leaving the other eye open for control. At the imaging day (day 14 for chick and day 80 for guinea pigs), the eyes were imaged in vivo and then harvested for axial length measurement and histological validation. The preliminary results confirmed the potential biomarkers can be extracted from the measured scleral fiber structure information.

Figure 4:
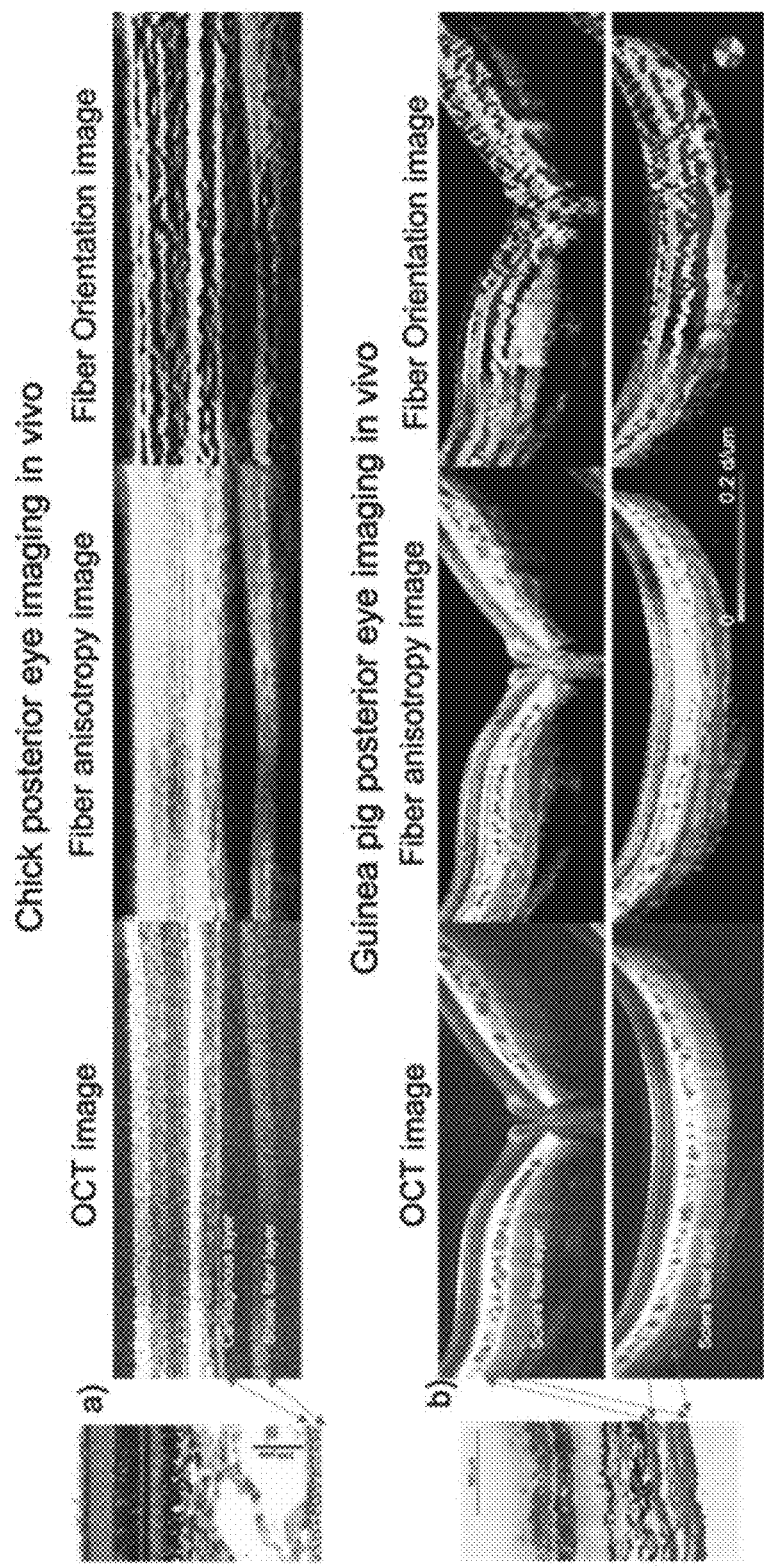
FIG. 4 shows representative cross-sectional images in a) chick and b) guinea pig models.

FIG. 4 shows representative cross-sectional images in a) chick and b) guinea pig, respectively. Histological validation was conducted to verify the sclera layer of interest. For the chick model, sclera has two layers, the cartilaginous layer and the collagen fiber layer. The two layers can be identified from OCT images and show distinctive features of high anisotropy and highly organized orientation. For the guinea pig model, the scleral layer can be seen clearly below the choroid and verified by histology. Fiber anisotropy and orientation further confirmed the collagen-rich scleral structure. The cross-sectional images can be stacked to render 3D images of the sclera fibre structure.

Figure 5:
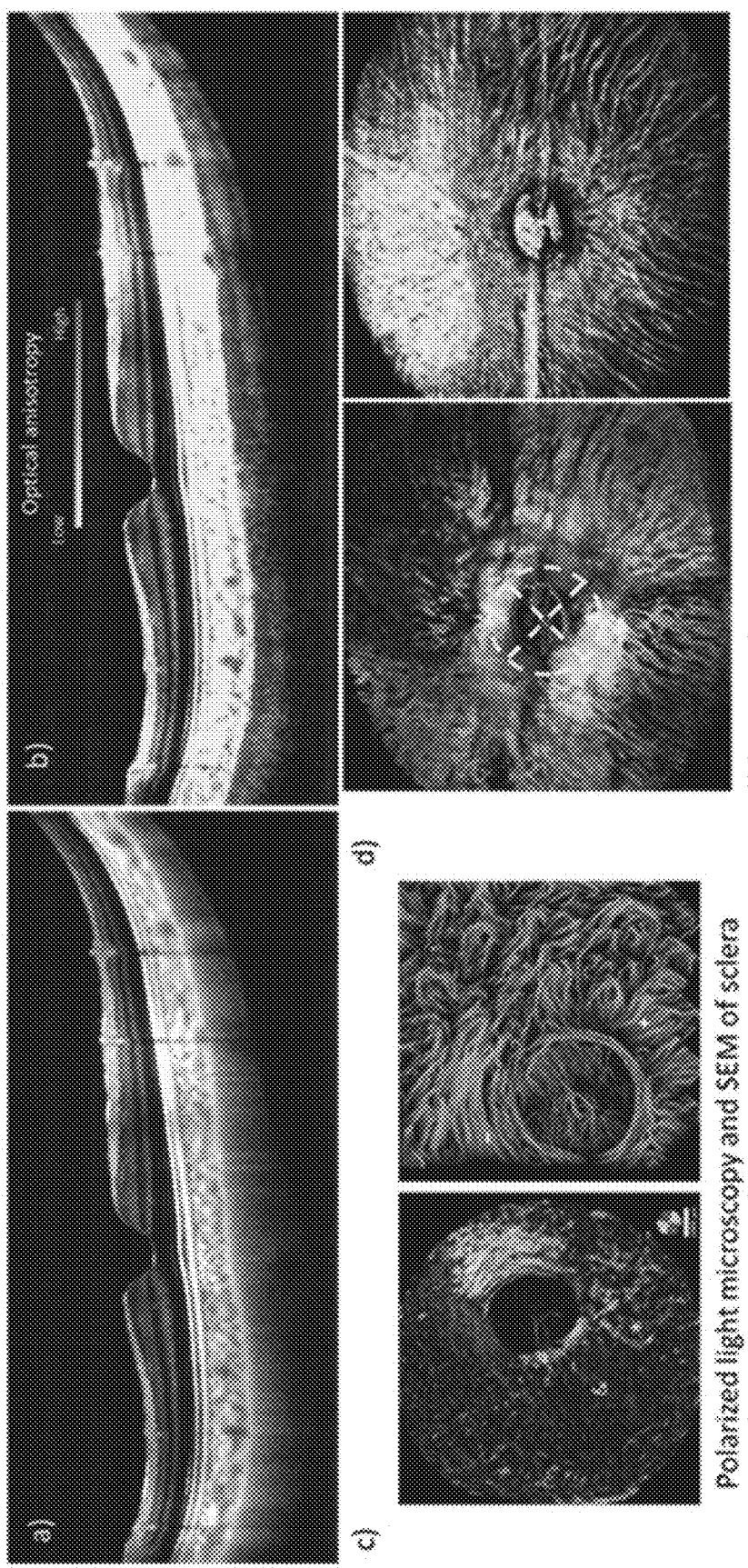
FIG. 5(a) shows an OCT image sliced from a volume scan.
FIG. 5(b) shows the reconstructed sclera anisotropy map for the image of FIG. 5(a)
FIG. 5(c) shows results obtained from prior art ex-vivo imaging techniques.
FIG. 5(d) shows collagen anisotropy maps derived using embodiments of the present disclosure.

FIG. 5 shows the result from a monkey in vivo. FIG. 5(a) shows intensity imaging of the fovea. FIG. 5(b) shows the reconstructed sclera fiber anisotropy. With the volume scanning, the scleral fiber architecture can be reconstructed. Circumferential, radial and tangential fiber structure can be seen from the images. The observation is consistent with previous reports based on ex vivo imaging techniques (FIG. 5(c)). Metrics can be derived from the present 3D measurement, including but not limited to collagen geometry and high resolution anisotropy maps (FIG. 5(d)).

Figure 6:
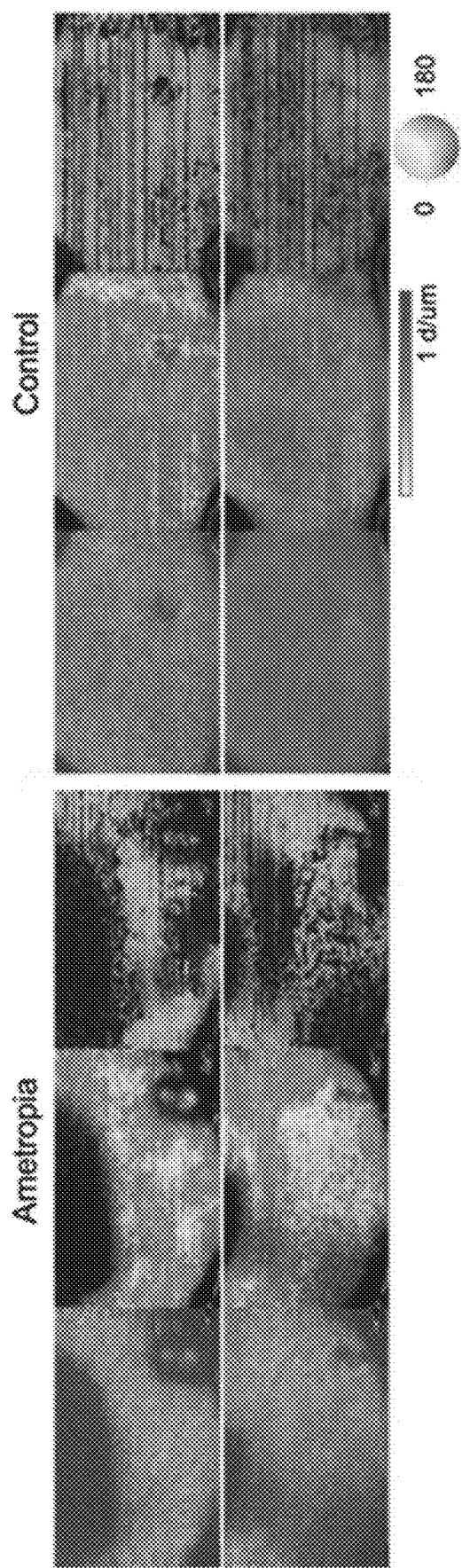
FIG. 6 shows representative en-face images of sclera structure in-vivo on defocused chick models.

FIG. 6 shows representative en-face images of sclera structure in vivo on defocused chick models. In the ametropic eye, the sclera (left panel) showed remodeling and the fiber structure was de-organized compared to the control image (right panel). The de-organization in collagen structure can be seen from the fiber anisotropy map evidenced by unevenly distributed anisotropy values. The de-organization was more obvious in the fiber orientation image, where a star-like orientation pattern in the ametropia eye was not seen in the control eye.

Figure 7:
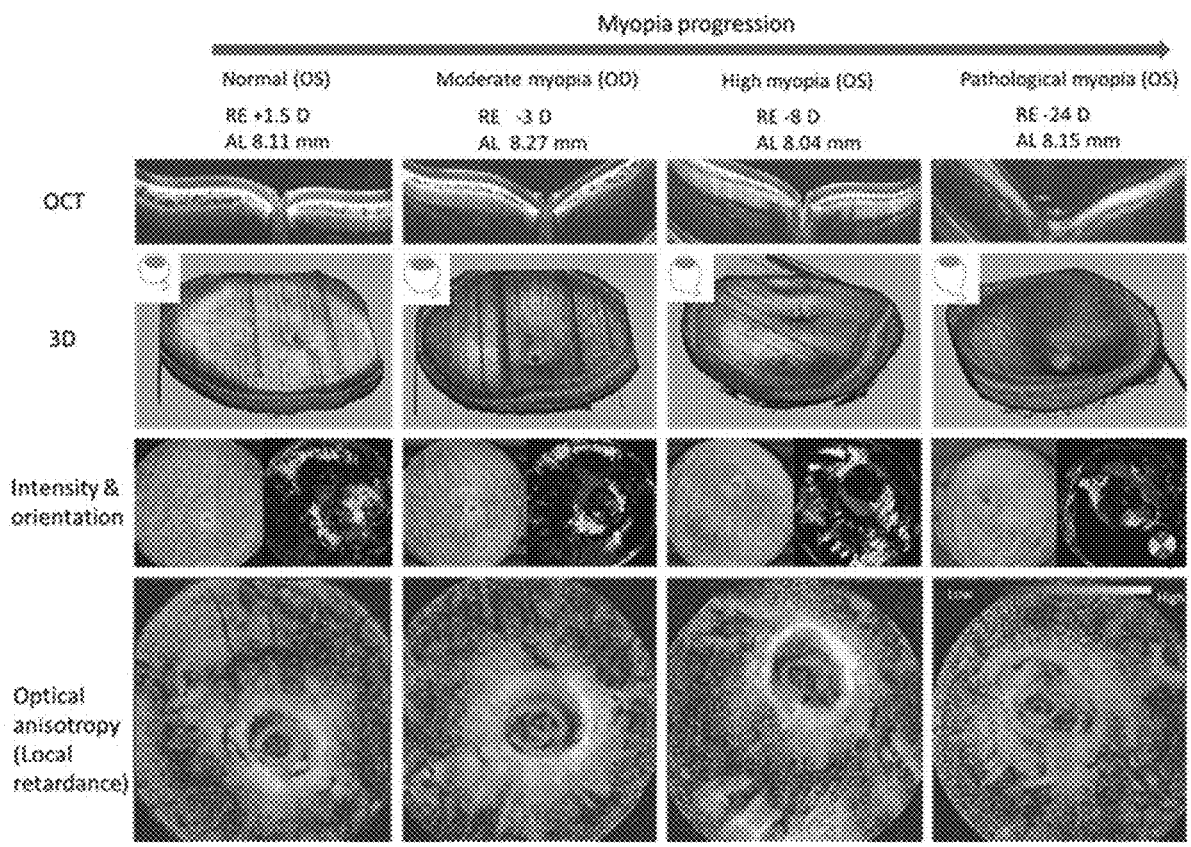
FIG. 7 shows OCT cross-section, 3D rendering with inset of a sketch of the eye shape, en-face intensity, fiber orientation and optical anisotropy images at different myopia stages in a myopia guinea pig model.

FIG. 7 shows imaging results from guinea pigs. A group of guinea pigs (Dunkin Hartley albino and Elm Hill pigmented) were bred on-site. Refractive development of each animal was measured every week using retinoscopy. At the age of 70 days, four guinea pigs (corresponding to the four columns in FIG. 7) representing different stages of myopia were selected. Animals were anesthetized with an intramuscular injection of a cocktail of Ketamine Hydrochloride and imaged with the PS-OCT system 100. The sclera was manually segmented and en-face images were produced by computing the average of the sclera tissue along the depth. The OCT cross-section, 3D rendering with inset of a sketch of the eye shape, en-face intensity, fiber orientation and optical anisotropy images at different myopia stages are shown in FIG. 7. Anatomical changes were observed, including thinning and enlarged curvature of the posterior sclera. It was also observed that the progression of myopia can be screened from the change in sclera collagen anisotropy maps. It was found that during the progression of myopia, the scleral fiber anisotropy increased. This may be due to the stretching of the posterior sclera during the elongation of the eye ball. Of interest, the scleral fiber anisotropy decreased to a lower value in staphyloma, differentiating the sclera condition from the non-pathological myopic eyes.

Figure 8:
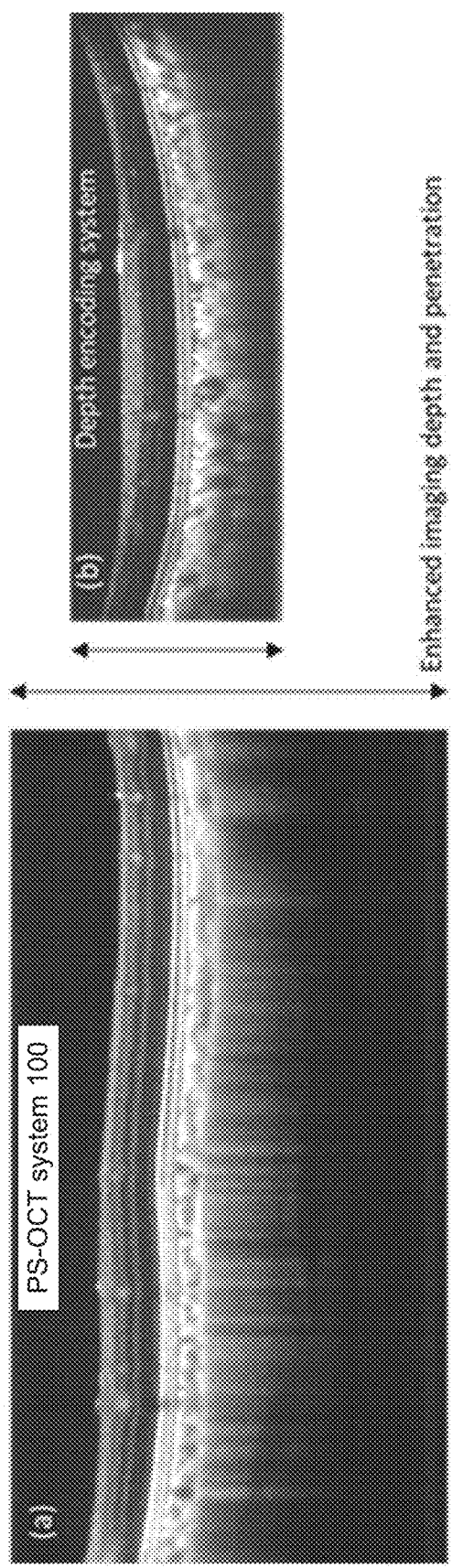
FIG. 8 shows a comparison between images on monkey retina in-vivo: (a) image generated by an embodiment of the present disclosure; (b) image generated by a polarization depth encoding system according to the prior art.

FIG. 8(a) shows a comparison between the PS-OCT system of embodiments of the present disclosure, and FIG. 8(b) shows a polarization depth encoding prior art system as described in PCT publication WO2010/054097. Compared to this prior art system, the present technology has an advantage in terms of imaging depth, sensitivity and penetration. With the same system parameters, the present technology has a doubled imaging depth and 2-5 dB better sensitivity (200-500 micrometres better penetration). Mechanically, the present technology is also more compact and robust.

Figure 9:
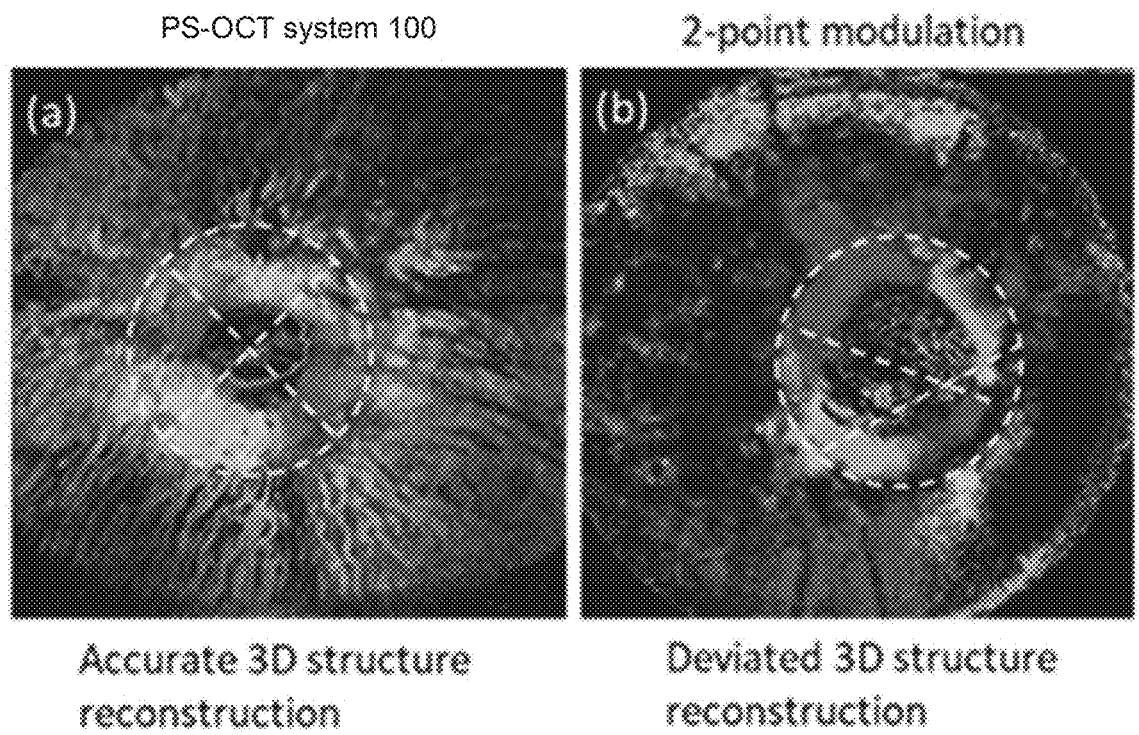
FIG. 9 shows a comparison between images on monkey retina in-vivo: (a) image generated using an embodiment of the present disclosure; (b) image generated using a 2-point modulation system according to prior art systems.

Other prior art systems use two-step modulation, compared to the three-step modulation of the present disclosure. The presently disclosed technology has an advantage over such prior art systems in terms of reliable measurement, due to full corneal compensation. With two-step modulation, interference from the cornea cannot be compensated, resulting in a deviated or even misleading structural result. An example is shown in FIG. 9. It can be seen that PS-OCT system 100 accurately reconstructs the 3D structure of the eye, as shown in FIG. 9(a), whereas deviations from the true structure are seen in FIG. 9(b).

Embodiments may have one or more of the following features and/or advantages:
  A modulation apparatus that can generate 3 eigen-polarization states in a high speed. This apparatus uses an electrical-optical modulator relatively positioned at an angle of 27.3678° to the fast axis of the modulator. This particular rotation angle of the polarizer enables generating all three eigen-polarization states. A 3-point step driving waveform is applied to the electrical-optical modulator to generate three eigen-polarization states.
  A swept source based polarization sensitive optical coherence tomography imaging system with enhanced ranging depth and sensitivity, which is capable of imaging the deep retina sclera.
  A method to computationally reconstruct the full Mueller matrix of the scleral collagen structural information using the measured data and a priori knowledge of the scleral architecture.
  A method to use depolarization properties to segment the sclera from the choroid and the noise signal arising from deep orbital structures.
  A method to quantify the measured data by tractographic processing and derive metrics that indicate the underlying physiological state of the subject's sclera. (ie. the collagen anisotropy).
  Derived metrics from the scleral volume measurement, including the collagen anisotropy of the posterior pole, can serve as new biomarkers for myopia screening, diagnosis, risk stratification, treatment monitoring and as surrigate outcome for clinical trials as well as for other diseases including the sclera such as glaucoma or posterior scleritis.

Many modifications will be apparent to those skilled in the art without departing from the scope of the present invention.

Throughout this specification, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

One or more embodiments of the invention are disclosed in the following numbered statements:
  1. A system for polarization-sensitive optical coherence tomography (PS-OCT) of a sample, comprising:

an interferometric arrangement comprising a reference arm and a sample arm, the sample arm being arranged to emit optical radiation towards the sample;
a phase modulation system arranged at an input to the sample arm; and
a detector arranged to detect a signal generated by interference between a reference beam from the reference arm and a sample beam from the sample arm;
wherein the phase modulation system comprises:
an electro-optic modulator;
a polarizer arranged at a rotation angle relative to the fast axis of the electro-optic modulator; and
a signal generator for delivering a driving voltage to the electro-optic modulator;
wherein the rotation angle and the driving voltage are selected such that the phase modulation system generates three mutually orthogonal polarization states.

2. A system according to 1, wherein the rotation angle is between about 17.6 degrees and about 38.1 degrees.

3. A system according to 2, wherein the rotation angle is 27.3678 degrees.

4. A system according to any one of 1 to 3, wherein the driving voltage has a sawtooth waveform.

5. A system according to 4, wherein the sawtooth waveform is a 3-point step driving waveform, the steps corresponding to modulation depths of −120 degrees, 0 degrees, and 120 degrees.

6. A system according to any one of 1 to 5, wherein the detector comprises a polarization diversity detection unit (PDDU).

7. A system according to any one of 1 to 6, comprising at least one processor that is configured to determine the Mueller matrix of the sample from the signal detected by the detector.

8. A system according to 7, wherein the at least one processor is configured to determine a diattenuation contribution to the Mueller matrix by polar decomposition.

9. A system according to 7 or 8, wherein the at least one processor is configured to determine birefringence of the sample based on the Mueller matrix.

10. A system according to 9, wherein the at least one processor is configured to apply a constraint to the determination of the birefringence of the sample based on a priori knowledge of one or more structural parameters of the sample.

11. A phase modulation system for polarization-sensitive optical coherence tomography (PS-OCT) of a sample, the phase modulation system being positionable at an input of a sample arm that is arranged to emit optical radiation towards the sample, the phase modulation system comprising:
an electro-optic modulator;
a polarizer arranged at a non-zero rotation angle relative to the fast axis of the electro-optic modulator; and
a signal generator for delivering a driving voltage to the electro-optic modulator;
wherein the rotation angle and the driving voltage are selected such that the phase modulation system generates three mutually orthogonal polarization states.

12. A phase modulation system according to 11, wherein the rotation angle is between about 17.6 degrees and about 38.1 degrees.

13. A phase modulation system according to 12, wherein the rotation angle is 27.3678 degrees.

14. A phase modulation system according to any one of 11 to 13, wherein the driving voltage has a sawtooth waveform.

15. A phase modulation system according to 14, wherein the sawtooth waveform is a 3-point step driving waveform, the steps corresponding to modulation depths of −120 degrees, 0 degrees, and 120 degrees.

16. A method of polarization-sensitive optical coherence tomography (PS-OCT) of a sample, comprising:
generating, by sample arm optics, a sample beam for illuminating the sample; and
detecting an interference signal generated by interference of the sample beam with a reference beam;
wherein the sample arm optics have a phase modulation system arranged at an input thereof, the phase modulation system being configured to:
transmit an input beam through a polarizer arranged at a rotation angle relative to the fast axis of an electro-optic modulator; and
deliver a driving voltage to the electro-optic modulator;
wherein the rotation angle and the driving voltage are selected such that the phase modulation system generates three mutually orthogonal polarization states.

17. A method according to 16, wherein the rotation angle is between about 17.6 degrees and about 38.1 degrees.

18. A method according to 17, wherein the rotation angle is 27.3678 degrees.

19. A method according to any one of 16 to 18, wherein the driving voltage has a sawtooth waveform.

20. A method according to 19, wherein the sawtooth waveform is a 3-point step driving waveform, the steps corresponding to modulation depths of −120 degrees, 0 degrees, and 120 degrees.

21. A method according to any one of 16 to 20, wherein the interference signal is detected by a polarization diversity detection unit (PDDU).

22. A method according to any one of 16 to 21, comprising determining the Mueller matrix of the sample from the interference signal.

23. A method according to 22, comprising determining a diattenuation contribution to the Mueller matrix by polar decomposition.

24. A method according to 22 or 23, comprising determining birefringence of the sample based on the Mueller matrix.

25. A method according to 24, comprising applying a constraint to the determination of the birefringence of the sample based on a priori knowledge of one or more structural parameters of the sample.

26. A method according to any one of 16 to 25, wherein the sample is an eye.

27. A method according to 26, further comprising generating a fiber anisotropy image and/or a fiber orientation image of the sclera of the eye.

28. A method according to 27 when appended to 25, wherein the constraint is that the fiber collagen is circumferential around the optical nerve head on the sclera.

29. A method of modulating a sample beam for polarization-sensitive optical coherence tomography (PS-OCT) of a sample, comprising:

arranging a phase modulation system at an input of sample arm optics of a PS-OCT system, the phase modulation system being configured to:
  transmit an input beam through a polarizer arranged at a rotation angle relative to the fast axis of an electro-optic modulator; and
  deliver a driving voltage to the electro-optic modulator;
  wherein the rotation angle and the driving voltage are selected such that the phase modulation system generates three mutually orthogonal polarization states.

30. A method according to 29, wherein the rotation angle is between about 17.6 degrees and about 38.1 degrees.

31. A method according to 30 wherein the rotation angle is 27.3678 degrees.

32. A method according to any one of 29 to 31, wherein the driving voltage has a sawtooth waveform.

33. A method according to 32, wherein the sawtooth waveform is a 3-point step driving waveform, the steps corresponding to modulation depths of −120 degrees, 0 degrees, and 120 degrees.

The invention claimed is:

1. A system for polarization-sensitive optical coherence tomography (PS-OCT) of a sample, comprising:
  an interferometric arrangement comprising a reference arm and a sample arm, the sample arm being arranged to emit optical radiation towards the sample;
  a phase modulation system arranged at an input to the sample arm; and
  a detector arranged to detect a signal generated by interference between a reference beam from the reference arm and a sample beam from the sample arm;
  wherein the phase modulation system comprises:
    an electro-optic modulator;
    a polarizer arranged at a rotation angle relative to the fast axis of the electro-optic modulator; and
    a signal generator for delivering a driving voltage to the electro-optic modulator;
    wherein the rotation angle and the driving voltage are selected such that the phase modulation system generates three mutually orthogonal polarization states.

2. A system according to claim 1, wherein the rotation angle is between about 17.6 degrees and about 38.1 degrees.

3. A system according to claim 2, wherein the rotation angle is 27.3678 degrees.

4. A system according to claim 1, wherein the driving voltage has a sawtooth waveform.

5. A system according to claim 4, wherein the sawtooth waveform is a 3-point step driving waveform, the steps corresponding to modulation depths of −120 degrees, 0 degrees, and 120 degrees.

6. A system according to claim 1, comprising at least one processor that is configured to determine the Mueller matrix of the sample from the signal detected by the detector.

7. A system according to claim 6, wherein the at least one processor is configured to determine birefringence of the sample based on the Mueller matrix.

8. A system according to claim 7, wherein the at least one processor is configured to apply a constraint to the determination of the birefringence of the sample based on a priori knowledge of one or more structural parameters of the sample.

9. A phase modulation system for polarization-sensitive optical coherence tomography (PS-OCT) of a sample, the phase modulation system being positionable at an input of a sample arm that is arranged to emit optical radiation towards the sample, the phase modulation system comprising:
  an electro-optic modulator;
  a polarizer arranged at a non-zero rotation angle relative to the fast axis of the electro-optic modulator; and
  a signal generator for delivering a driving voltage to the electro-optic modulator;
  wherein the rotation angle and the driving voltage are selected such that the phase modulation system generates three mutually orthogonal polarization states.

10. A phase modulation system according to claim 9, wherein the rotation angle is between about 17.6 degrees and about 38.1 degrees.

11. A phase modulation system according to claim 10, wherein the rotation angle is 27.3678 degrees.

12. A method of polarization-sensitive optical coherence tomography (PS-OCT) of a sample, comprising:
  generating, by sample arm optics, a sample beam for illuminating the sample; and
  detecting an interference signal generated by interference of the sample beam with a reference beam;
  wherein the sample arm optics have a phase modulation system arranged at an input thereof, the phase modulation system being configured to:
    transmit an input beam through a polarizer arranged at a rotation angle relative to the fast axis of an electro-optic modulator; and
    deliver a driving voltage to the electro-optic modulator;
    wherein the rotation angle and the driving voltage are selected such that the phase modulation system generates three mutually orthogonal polarization states.

13. A method according to claim 12, wherein the rotation angle is between about 17.6 degrees and about 38.1 degrees.

14. A method according to claim 13, wherein the rotation angle is 27.3678 degrees.

15. A method according to claim 12, wherein the driving voltage has a sawtooth waveform.

16. A method according to claim 15, wherein the sawtooth waveform is a 3-point step driving waveform, the steps corresponding to modulation depths of −120 degrees, 0 degrees, and 120 degrees.

17. A method according to claim 12, comprising determining the Mueller matrix of the sample based on the interference signal.

18. A method according to claim 17, comprising determining birefringence of the sample based on the Mueller matrix.

19. A method according to claim 18, comprising applying a constraint to the determination of the birefringence of the sample based on a priori knowledge of one or more structural parameters of the sample.

20. A method according to claim 19, wherein the sample is an eye, and wherein the method further comprises generating a fiber anisotropy image and/or a fiber orientation image of the sclera of the eye.

21. A method according to claim 20, wherein the constraint is that the fiber collagen is circumferential around the optical nerve head on the sclera.

* * * * *